United States Patent [19]

Okumoto

[11] Patent Number: 4,766,910

[45] Date of Patent: Aug. 30, 1988

[54] CONTENT TOBACCO AMOUNT CONTROLLING DEVICE FOR A CIGARETTE MAKING MACHINE

[75] Inventor: Yutaka Okumoto, Musashino, Japan

[73] Assignee: Japan Tobacco Inc., Tokyo, Japan

[21] Appl. No.: 705,877

[22] Filed: Feb. 26, 1985

[30] Foreign Application Priority Data

May 8, 1984 [JP] Japan ................................ 59-90256

[51] Int. Cl.[4] ................................ A24C 5/14

[52] U.S. Cl. ................................ 131/84.1; 131/84.4; 131/905; 131/906; 131/908

[58] Field of Search ............... 131/905, 906, 788, 908, 131/84.1, 84.4

[56] References Cited

U.S. PATENT DOCUMENTS 4,063,563 12/1977 Lorenzen ........................ 131/84.4
4,306,573 12/1981 Rudszinai ........................ 131/84.4
4,474,190 10/1984 Brand ........................ 131/84.4
4,595,027 6/1986 Higgins et al. ........................ 131/84.4

*Primary Examiner*—V. Millin
*Attorney, Agent, or Firm*—Murray and Whisenhunt

[57] ABSTRACT

A content tobacco amount controlling device for use with a cigarette making machine of the type including a cigarette conveyor, a tobacco trimming device, and a tobacco wrapping device. The controlling device includes first and second radio ray density detecting devices, and a first integrator connected to the second radio ray density detecting device for integrating an electric signal from the second radio ray density detecting device. An adding device is connected to the first integrator, and a second integrator is connected to the adding device for integrating an output of the adding device. The trimming device is operated in response to an output of the second integrator to control the amount of content tobacco after trimming.

1 Claim, 8 Drawing Sheets

F I G. 1
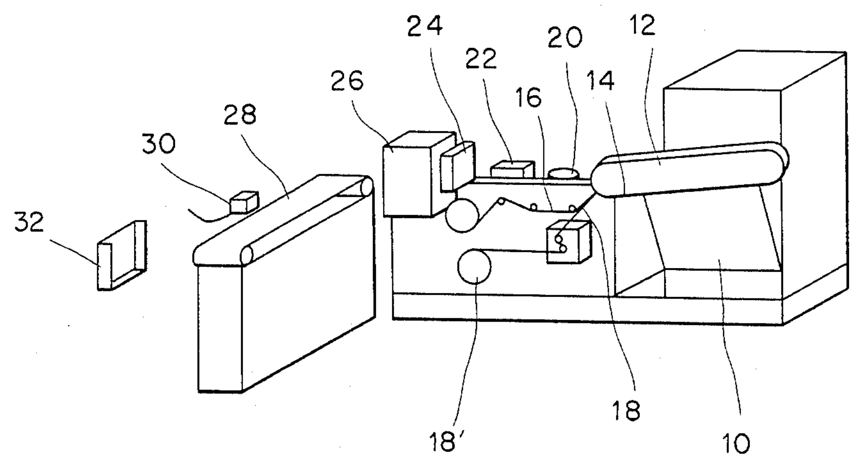

F I G. 2
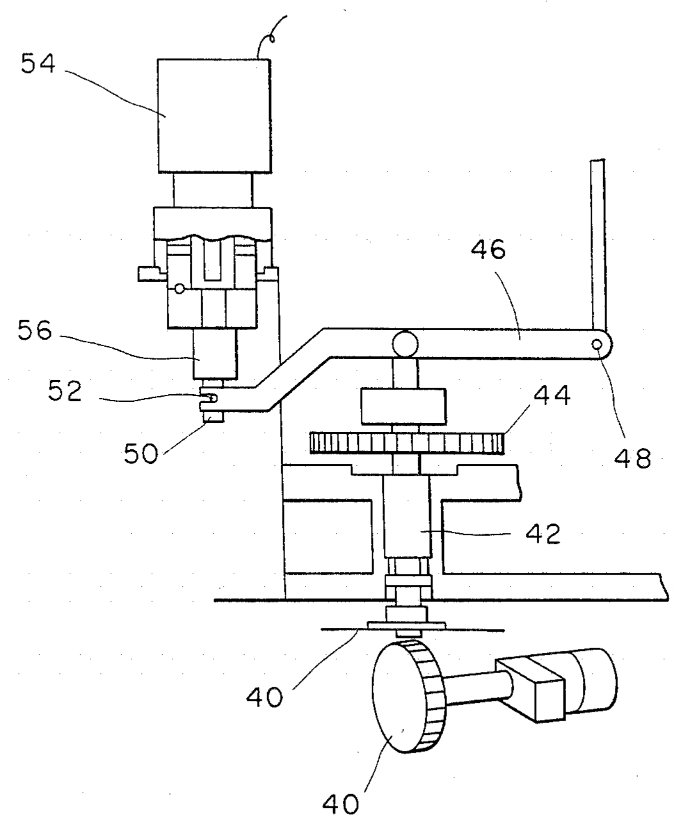

54
78b
80b
78
80
78a
80a
76c
76
76a
76b
74
72
64
70
62
68
60
66

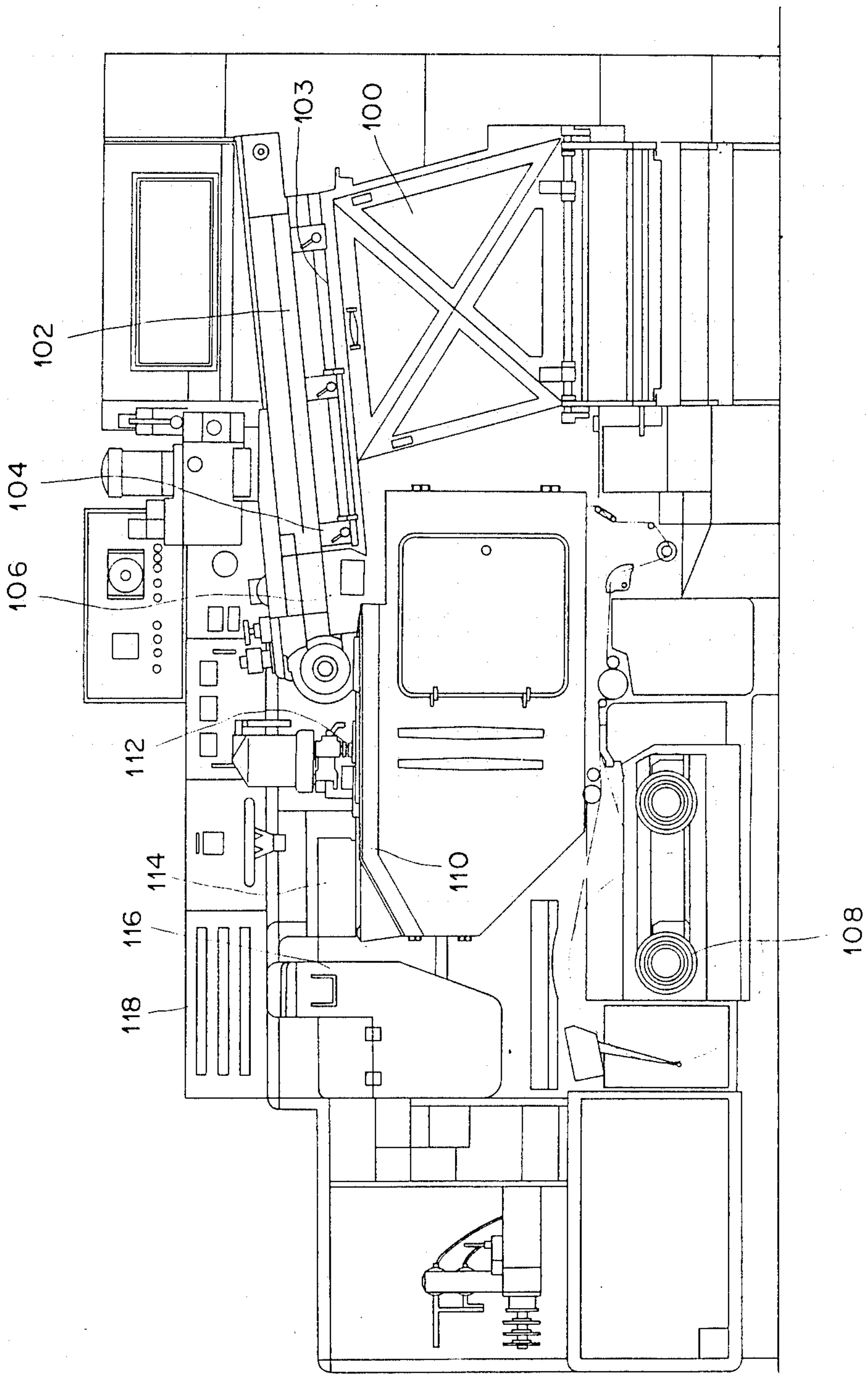
F I G . 4
100
102
103
104
106
108
110
112
114
116
118

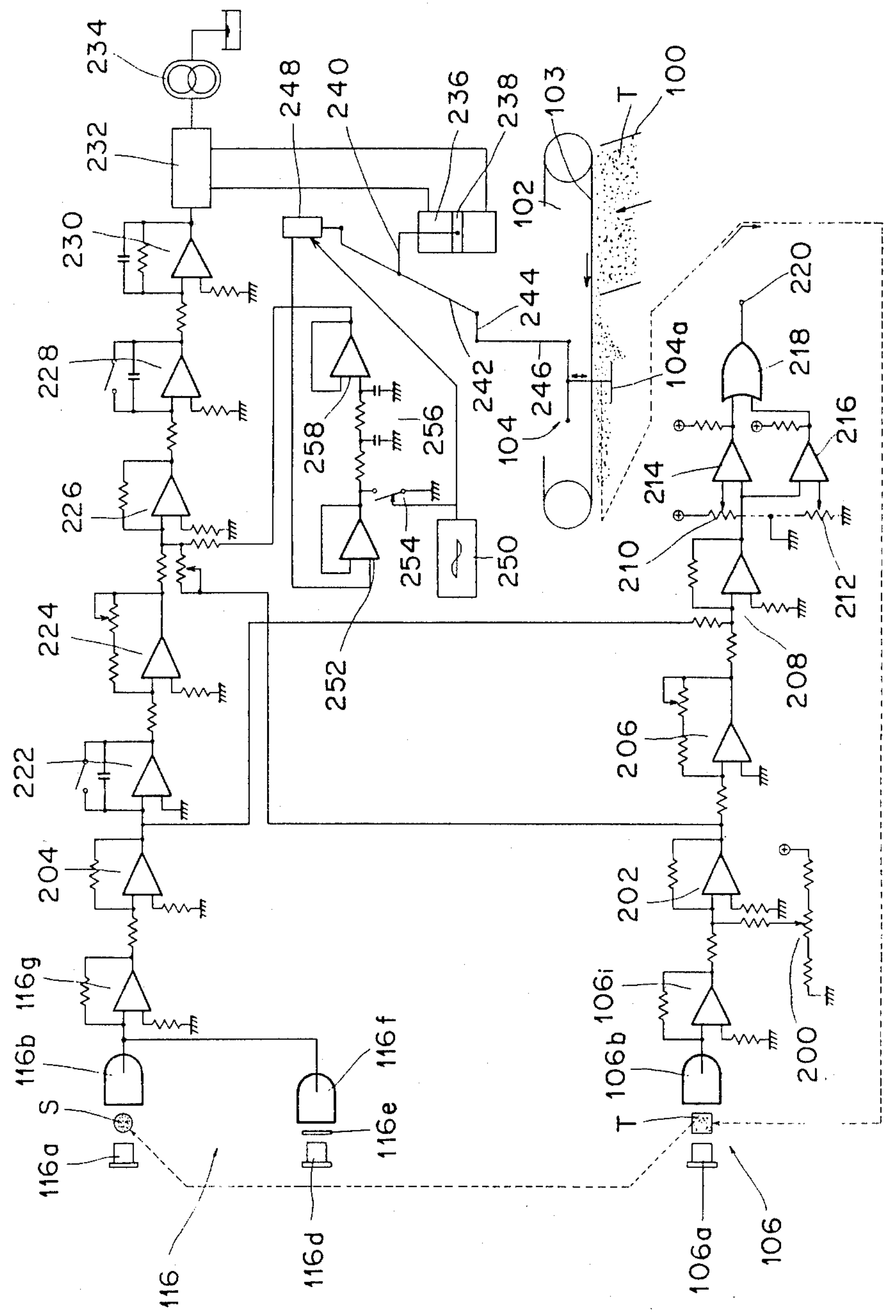
F I G . 7
234
232
248
240
236
238
103
T
100
102
230
228
226
224
222
204
116g
116b
S
116a
116
116d
116e
116f
244
242
246
104
104a
220
218
216
214
210
212
208
206
202
200
106i
106b
T
106a
106
258
256
254
250
252

CONTENT TOBACCO AMOUNT CONTROLLING DEVICE FOR A CIGARETTE MAKING MACHINE

BACKGROUND OF THE INVENTION

This invention relates to a content tobacco amount controlling device for a cigarette making machine, and more particularly to a content tobacco amount controlling device for maintaining amounts of content tobacco constant to assure desired average and uniform amounts of content tobacco.

It is very important for cigarette producers to reduce costs of cigarettes to be produced in order to increase the profits to be obtained therefrom, and great efforts have been made to attain this.

One of solutions to reduce production costs is to improved the productivity of a cigarette making machine, and at present, cigarette making machines which can produce up to 8,000 cigarettes per minute are being put to practical use.

Another solution to reduce production costs is to reduce variations of weight of content tobacco in individual cigarettes to be produced.

In particular, since the price of leaf tobacco has made a sudden rise lately, if only a small amount of content tobacco can be reduced from each cigarette, a vast amount of profit can be yielded thereby. However, if content tobacco is reduced by too large an amount, cigarettes to be produced cannot preserve predetermined quality. Accordingly, variations of weight of content tobacco of cigarettes are measured and a standard deviation thereof is determined statistically so that, when cigarettes are to be produced, they may have an aimed weight provided by a minimum allowable weight as accepted products added by an amount proportional to a variation of weight of content tobacco of cigarettes so as to yield little rejected cigarettes.

In other words, reduction of variations of weight of content tobacco of cigarettes will be attained by reduction of the aimed value of weight. This is the very reason why cigarette producers make great efforts to reduce variations of weight of content tobacco of cigarettes.

While it is important to maintain cigarette making machines sufficiently to try to reduce plays thereof arising from abrasion in order to reduce variations of amounts of content tobacco of cigarettes, the best solution is to provide a cigarette making machine additionally with a content tobacco amount controlling device of high performance. To this end, various systems have been proposed and put into practical use so far.

One of such systems is disclosed in Japanese Pat. Appln. Pub. No. 38-18750. This system makes use of the fact that there is some correlation between a weight of shredded tobacco and air permeability to control an amount of content tobacco using the air permeability as an index. This system, however, was not able to reduce deviations of amounts of content tobacco of cigarettes very much since it is influenced from a fluctuation of pressure at a sucking source and a grain size and composition of shredded tobacco so that the correlation between the weight of shredded tobacco and the permeability.

Another one of the systems is disclosed in U.S. Pat. Nos. 2,937,280 and 2,861,683. This system makes use of the fact that there is some correlation between an amount of shredded tobacco and the electrostatic capacity and uses the electrostatic capacity as an index. However, since this system is apt to be influenced from the water or temperature of shredded tobacco to disturb the correlation between the weight of shredded tobacco and the electrostatic capacity, it is not effective to reduce variations of amounts of content tobacco of cigarettes. Accordingly, this system is hardly put into practical use.

A further one of the systems makes use of the fact that there is some correlation between radio rays, particularly beta rays emitted from strontium 90, and the density of shredded tobacco to control the amount of shredded tobacco using the permeability of shredded tobacco to the radio rays. Since this system handles radio rays, it involves a problem of assuring the safety and another problem of a drift and responsiveness of an amplifier at a latter stage arising from the fact that an electric current outputted from an ion box which forms a detecting means is very weak. However, since a very good correlation exists between the permeability to radio rays and the density of shredded tobacco, this system is employed in almost all of cigarette making machines at present to detect an amount of content tobacco.

Meanwhile, Japanese Publication Patent No. 39-9450 discloses a system which includes a radio ray detector to provide a signal for controlling an amount of content tobacco of a cigarette to be produced by a cigarette making machine. However, since this system is designed to obtain a desired amount of content tobacco by controlling the speed of a feeder for shredded tobacco, the entire system becomes large-scaled and the responsiveness becomes low. Accordingly, the system has been seldom put into practical use.

A device which employs a radio ray detector to control an amount of content tobacco of a cigarette is also disclosed in Japanese Publication Patent No. 36-16250. In this system, the speed of a conveyor for shredded tobacco is regulated to obtain a desired amount of content tobacco and is thus superior to the system which is designed to regulate the speed of an entire feeder. However, this system is also inferior in the responsiveness and hence has not been put into practical use as yet.

Japanese Pat. Appln. Pub. No. 39-15949 discloses a different system which involves control utilizing air permeability and control using a radio ray density detector. In this system, a signal provided from the radio ray density detector is processed to move a trimmer up and down to vary an amount of content tobacco to be contained in a cigarette. Since responsiveness of this system is thus very quick comparing with the systems disclosed in Japanese Pat. Appln. Pub. No. 39-9450 and No. 36-15250 described above, this system is employed in almost all of cigarette making machines at present.

An example of the system in which a trimmer is moved up and down by means of a motor will be described below with reference to FIGS. 1 to 3.

Referring first to FIG. 1 is a perspective view showing a general construction of a cigarette making machine, shredded tobacco is attracted into and moved up within a chimney 10 and is then attracted into a layer on a bottom face of a perforated cigarette conveyor located at the bottom of a suction chamber 12. The shredded tobacco thus layered is carried in a leftward direction in FIG. 1 and is adjusted into a layer of a suitable thickness by means of a trimming device 14. The shredded tobacco of the adjusted layer thickness is transferred onto wrapping paper 18 placed on a cloth tape 16 and is wrapped into the wrapping paper 18 here. The wrapping paper 18 in which the shredded tobacco is wrapped is pasted by means of a pasting device 20 and is dried into a bar-like cigarette by a heater 22. Reference numeral 18' designates a wrapping paper supply roll.

The bar-like cigarette thus formed is passed through a radio ray density detector 24 to measure the density of content tobacco and is then cut into separate cigarettes by a cutter 26. The separately cut cigarettes are transferred onto and transported by a conveyor 28, and during such transportation, rejected products are removed by a magnet valve 30 to allow only accepted products to be loaded onto a tray 32.

Referring now to FIG. 2 which illustrates an example of the trimming device, a trimming disk 40 is secured to an end of a shaft 42 so that it may be rotated by way of a gear 44 mounted on the other end of the shaft 42. The trimming disk 40 is vertically positioned by a link 46 which is in turn positioned by moving either one of fulcra 48 and 50. A nut 52 is secured at the fulcrum 50, and a threaded portion of a rotary shaft 56 of a motor 54 is screwed in the nut 52. The motor 54 can rotate in opposite directions, and as the motor 54 is rotated in a forward or reverse direction, the link 46 is moved up or down relative to the fulcrum 48 to move up or down the disk 40. A thickness of a layer of shredded tobacco which passes this station is varied in response to up or down movement of the disk 40.

Referring to FIG. 3 which illustrates a circuit for driving the motor 54 to rotate alternatively in the forward or reverse direction, radio rays emitted from a radio ray source 60, for example, beta rays emitted from strontium 90, pass through a bar-like cirgarette 62 and are thrown into an ion box 64. If the density of content tobacco of the cigarette 62 is then high, the number of radio rays received by the ion box is reduced so that an ionization current produced by the ion box 64 is reduced. Meanwhile, radio rays emitted from another radio ray source 66 are passed through a standard density body 68 and is thrown into another ion box 70 which thus produces a standard ionization current.

Normally, positive and negative voltages are applied to the ion boxes 64 and 70, respectively, as seen in FIG. 3, and hence ionization currents of opposite polarity are generated at the ion boxes 64 and 70. Accordingly, if the density of content tobacco of a bar-like cigarette 62 to be measured is equal to that of a standard one, an output of an amplifier 72 is zero. Meanwhile, if the density of the bar-like cigarette 62 is higher than the standard density, an ionization current produced at the ion box 64 is lower in an absolute value than an ionization current produced at the ion box 70, and hence an electric current flows through a high resistor 74 so that the amplifier 72 provides a negative output therefrom. On the contrary, if the density of the bar-like cigarette 62 is lower than the standard density, the amplifier provides a positive output.

An averaging circuit 76 for averaging the output of the amplifier 72 includes an amplifier 76a and a negative feedback circuit therefore including a resistor 76c and a capacitor 76b connected in parallel to the resistor 76c.

Motor driving circuits 78 and 80 are connected to the motor 54, and when a signal averaged by the averaging circuit 76 is lower than a predetermined level, the driving circuit 78 drives the motor 54 to rotate in a direction to lower the disk 40 so as to raise the density of the bar-like cigarette 62, and on the contrary when the density is higher and the averaged signal is lower than another predetermined level, the driving circuit 80 drives the motor 54 to rotate in a direction to lift the disk 40 so as to lower the density of the bar-like cigarette 40. In this way, the density of bar-like cigarettes is adjusted to be maintained constant. Each of the motor driving circuits 78 and 80 includes a comparator 78a or 80a and a driver transistor 78b or 80b.

More particularly, upward or downward movement of the trimmer disk 40 is attained by forward or reverse rotation of the motor 54 in response to a result of determination whether an average in density over the length of a bar-like cigarette corresponding up to 50 cut cigarettes is higher or lower than a desired or aimed value. Accordingly, a desired responding speed cannot always be attained by the system.

In consideration of such circumstances, a new controlling device which further improves the controlling performance is proposed in Japanese Patent Application Publication No. 51-95198.

The proposed controlling device includes a means for irradiating radio rays onto tobacco feed into a cigarette making machine and for measuring an amount of radio rays passing through the tobacco to detect a density of the tobacco and convert the same into a corresponding electric signal, trimming means including a trimming disk for removing an excessive amount of shredded tobacco fed on a conveyor belt to adjust a cross sectional size of content tobacco, a piston means operated to move back and forth by pressure fluid from a pressure fluid distributor for moving the trimming disk up and down, and an electric hydraulic servo mechanism responsive to an electric signal from the means for outputting an electric signal proportional to an amount of radio rays passing through tobacco for operating the liquid pressure distributor, the electric signal having a negative feedback thereto of a vertical displacement of the trimming disk via a differential transformer. The proposed controlling device is improved particularly in the responding speed comparing with a device of the type including a motor to effect required controlling as described above.

Concretely, a ratio between a deviation of an average amount of content tobacco of cigarettes when controlled and a deviation of an average amount of content tobacco of cigarettes when not controlled, which ratio is regarded as an aim of an amount controlling performance, is 1/1.5 with the device using a motor while it is $\frac{1}{4}$ with the last described device, providing particular improvement in the performance. Thus, it has been made sure that when the last described device is applied to a cigarette making machine having a capacity to produce 4,000 to 5,000 cigarettes per minute, higher effects than those attained by a controlling device of the type wherein a trimming disk is moved up and down by a motor where it is installed for a cigarette making machine having a capacity to produce 2,000 cigarettes per minute can be attained. Accordingly, the last described device is widely put into practical use.

However, where a cigarette making machine has a capacity to produce 8,000 cigarettes per minute, a content tobacco amount controlling device having quicker responsiveness is required.

Accordingly, the last mentioned Japanese laid-open patent application further proposes a device comprising trimming means including a trimming disk for removing an excessive amount of shredded tobacco fed on a conveyor band to adjust a cross sectional size of content tobacco, compressing means located adjacent the trimming disk for compressing shredded tobacco fed thereto against the conveyor band to remove a gap between the shredded tobacco and the conveyor band, means for irradiating radio rays to a portion of the shredded tobacco positioned between the compressing means and the conveyor band and for measuring an amount of radio rays passing through the tobacco to detect the density of the shredded tobacco and convert the same into a corresponding electric signal, a piston means operated to move back and forth by pressure liquid from a pressure liquid distributor for moving the trimming disk up and down, and an electric hydraulic servo mechanism responsive to an electric signal from the means for outputting an electric signal proportional to an amount of radio rays passing through tobacco for operating the liquid pressure distributor, the electric signal having a negative feedback thereto of a vertical displacement of the trimming disk via a differential transformer. It is confirmed that, with this device, the aforementioned ratio is about ⅛, proving an extremely high performance.

The device of the proposal has a few drawbacks, too. In particular, if the radio ray density detector is installed in the neighborhood of a trimming device 14 (FIG. 1) in order to effect controlling of an amount of content tobacco of cigarettes, a slight difference appears between a signal from the density detector and another signal from a radio ray density detector 24 (FIG. 1) for measuring after cigarette rods are formed. Normally, the difference is 0.5 to 1% or so, but it cannot be ignored at present days in which management of content tobacco of higher accuracy is required.

A reason why such a difference appears is that a signal obtained by measurement by the radio ray density detector before cigarette rods are formed contains a component caused by an amount of shredded tobacco which has passed out of holes of a perforated cigarette conveyor on the bottom of a suction chamber 12 (FIG. 1) before the shredded tobacco is wrapped into wrapping paper after the measurement by the radio ray density detector, and such an amount of shredded tobacco escaped causes a difference of the density when measured after cigarette rods are formed.

Accordingly, it is apparent that a most desirable content tobacco amount controlling device is such that a responding speed of control is the same as that in a device wherein a radio ray density detector is located directly behind a trimming disk while an aimed value of control is associated with a measured value by a radio ray density detector after cigarette rods are formed.

SUMMARY OF THE INVENTION

The present invention has been made to eliminate such drawbacks of the conventional content tobacco amount controlling devices, and it is an object of the invention to provide a content tobacco amount controlling device for a cigarette making machine wherein a responding speed in controlling an amount of content tobacco of cigarettes is as high as that where a radio ray density detector is installed within a suction chamber directly behind trimming means and an aimed value of control is controlled in accordance with a measure value after a bar-like cigarette is formed so that the aimed value of cigarettes produced may always be maintained properly during production of cigarettes by a cigarette making machine.

In order to attain the object described just above, according to the present invention, a content tobacco amount controlling device comprises a first radio ray density detecting means for irradiating radio rays to tobacco on a cigarette conveyor directly after the tobacco has been trimmed by a trimming device and for measuring an amount of radio rays passing through the tobacco to output an electric signal representative of a difference between a measured density of the tobacco and a reference density, a second radio ray density detecting means for irradiating radio rays to a bar-like cigarette made by a tobacco wrapping means and for measuring an amount of radio rays passing through the bar-like cigarette to output an electric signal respresentative of a difference between a measured density of the barlike cigarette and a reference density, a first integrating means for integrating an electric signal from the second radio ray density detecting means, an adding means for adding an output of the first integrating means to an output of the first radio ray density detecting means, and a second integrating means for integrating an output of the adding means, the trimming device being operated in response to an output of the second integrating means to control an amount of content tobacco after trimming.

BRIEF DESCRIPTION OF THE DRAWINGS

FIG. 1 is a perspective view illustrating a cigarette making machine employing a conventional controlling device.

FIG. 2 is a front elevational view showing essential part of the conventional controlling device;

FIG. 4 is a front elevational view illustrating a cigarette making machine employing a controlling device according to the present invention;

FIG. 7 is a circuit diagram illustrating an electric circuit for a controlling device according to the present invention.

DETAILED DESCRIPTION OF THE PREFERRED EMBODIMENT

Figure 3:
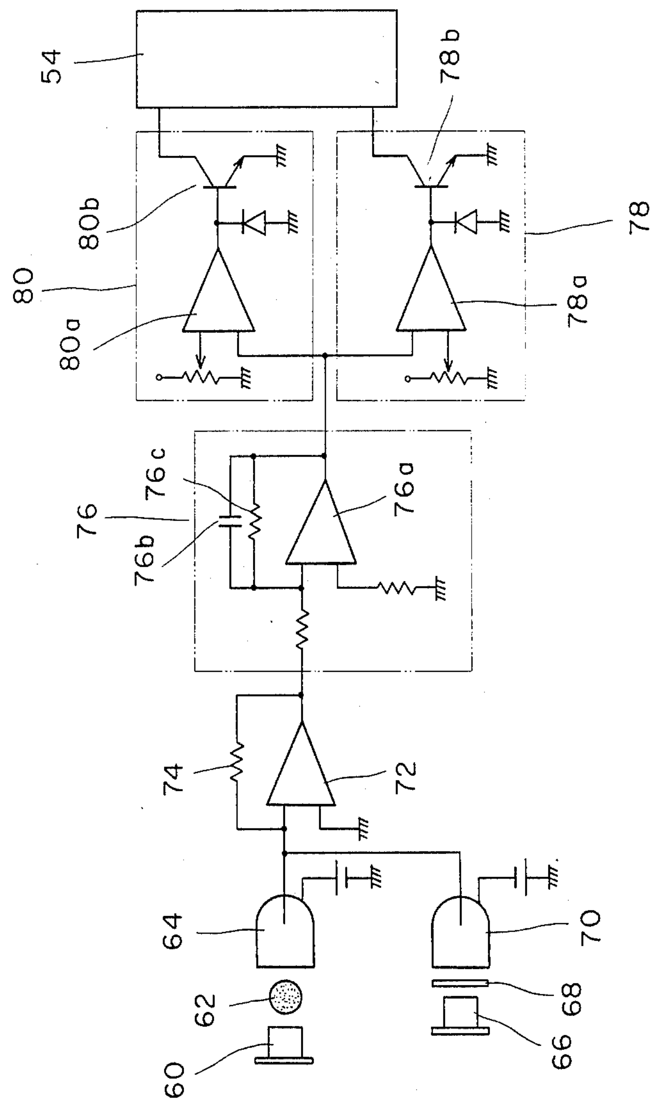
FIG. 3 is a circuit diagram illustrating an electric circuit of the conventional controlling device.

Now, a preferred embodiment of the present invention will be described in detail with reference to the accompanying drawings.

Referrring first to FIG. 4 which illustrates a cigarette making machine which employs a content tobacco amount controlling device according to the present invention, shredded tobacco is attracted into and moved up within a chimney 100 and is then attracted into a layer on a bottom face of a perforated cigarette conveyor located at the bottom of a suction chamber 102. The shredded tobacco thus layered is carried in a leftward direction in FIG. 4 and is adjusted into a layer of a suitable thickness by means of a trimming device 104. The shredded tobacco of the adjusted layer thickness is measured for density by a first radio ray density detector 106 located directly behind the trimming device 104 and is then transferred onto wrapping paper supplied from a wrapping paper roll and placed on a cloth tape 106 whereafter it is wrapped into the wrapping paper which is then pasted by means of a pasting device 112. The pasted portion of the wrapping paper is dried to form a bar-like cigarette by a heater 114. The bar-like cigarette thus formed is passed through a second radio ray density detector 116 to measure the density of content tobacco and is then cut into separate cigarettes by a cutter 118. The separately cut cigarettes are transferred onto and transported by a conveyor not shown in a similar manner as in case of the cigarette making machine shown in FIG. 1. Finally, the cigarettes are loaded onto a tray.

Figure 5:
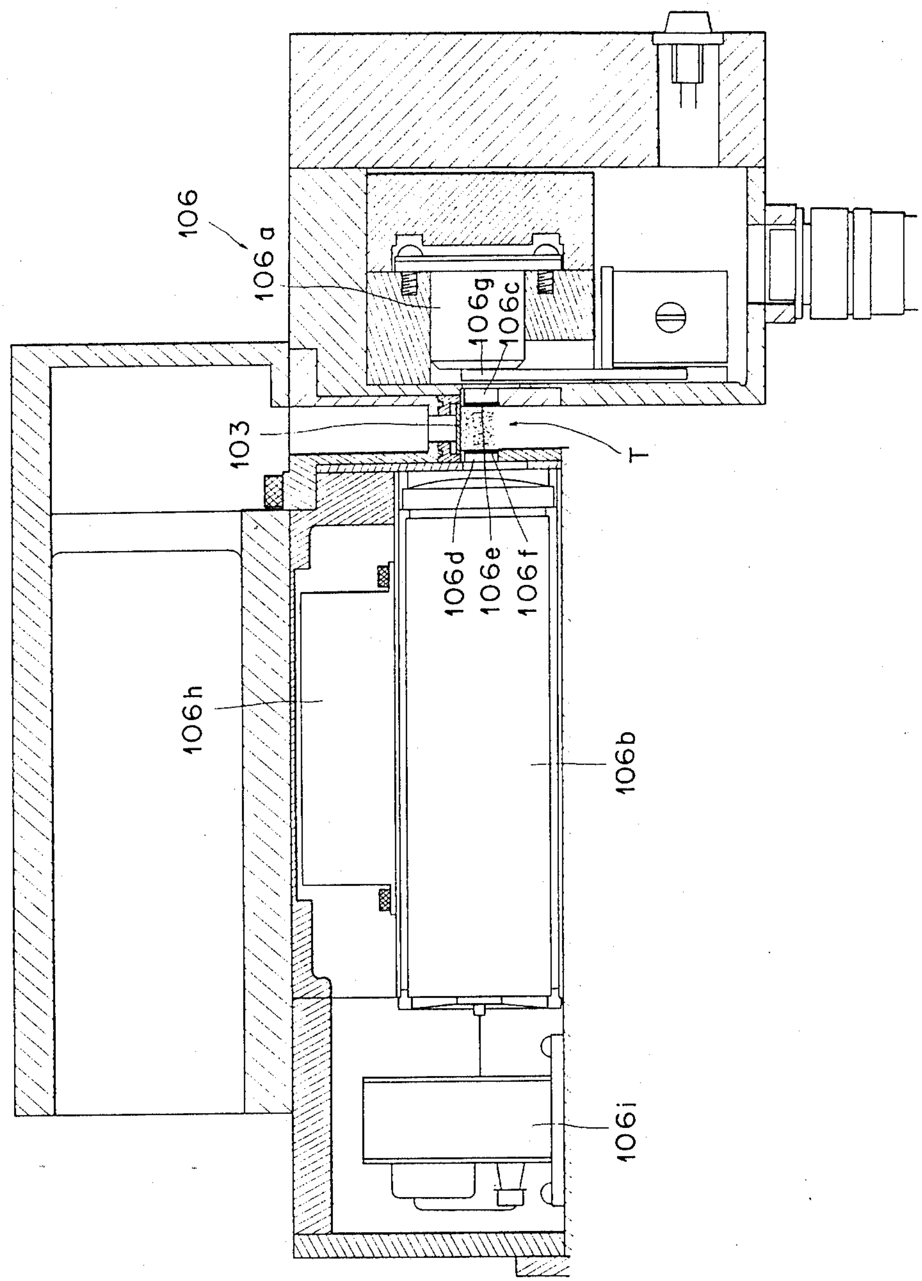
FIGS. 5 and 6 are enlarged cross sectional views of different portions of the machine of FIG. 4.

FIG. 5 illustrates a structure of the first radio ray density detector 106. The first radio ray density detector 106 includes a radio ray source 106*a* for emitting radio rays, and an ion box 106*b* for receiving radio rays from the radio ray source 106*a*. The radio ray source 106*a* and the ion box 106*b* are disposed in opposing relationship through window holes 106*c* and 106*d* perforated in respective casings which are located in a spaced relationship by a predetermined distance. Metal films 106*e* and 106*f* preferably made of titanium foil extend across the window holes 106*c* and 106*d*, respectively, and a channel through which shredded tobacco T on the perforated cigarette conveyor 103 passes after trimming is formed between the metal films 106*e* and 106*f*. A shutter 106*g* is located between the radio ray source 106*a* and the window hole 106*c* for preventing radio rays from inadvertently escaping externally therefrom when radio rays are not required.

In the arrangement of such a construction, radio rays from the radio rays source 106*a* pass, when the shutter 106*g* is open, through the metal film 106*e* in the window hole 106*c* and then through the shredded tobacco in the form of a layer and is then received by the ion box 106*b* via the metal film 106*f* in the window opening 106*d*. A high voltage is applied to an outer periphery of the ion box 106*b* from a high voltage power source 106*h* so that when the density of the shredded tobacco T is relatively high, a small electric current is supplied to an amplifier 106*i*, and on the contrary when the density of the shredded tobacco T is relatively low, a large electric current is supplied to the amplifier 106*i*. Accordingly, at an output of the amplifier 106*i*, a signal is obtained which represents the density of the layered shredded tobacco before it is wrapped into wrapping paper.

Figure 6:
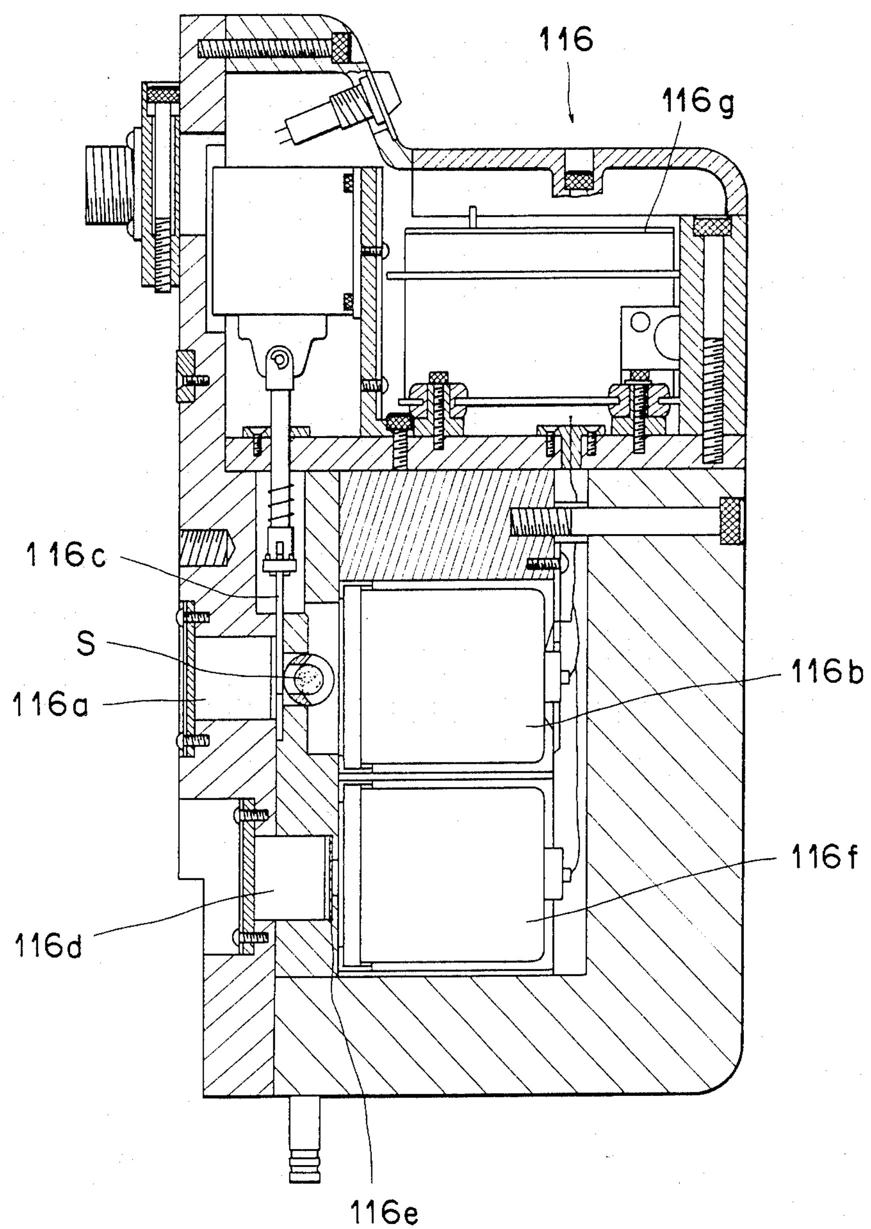

FIG. 6 illustrates a structure of the second radio ray density detector 116. As described hereinbefore, a detector of the type is already employed in most cigarette making machines. Radio rays emitted from the radio ray source 116*a* pass through a bar-like cigarette S and is received by the ion box 116*b*. When the density of the bar-like cigarette S is relatively high, an amount of radio rays passing through the cigarette S and received by the ion box 116*b* decreases so that an ionization current produced by the ion box 116*b* is reduced, and on the contrary when the density of the cigarette S is relative low, an amount of radio rays received by the ion box 116*b* increases so that an ionization current is also increased. A shutter 116*c* is provided for opening and closing operation between the radio ray source 116*a* and the cigarette S.

Another radio ray source 116*d* is located adjacent the radio ray source 116*a* such that radio rays from the radio ray source 116*d* may pass through a reference or standard density body 116*e* and be received by an ion box 116*f* so that a reference ionization current may be produced by the ion box 116*f*. Normally, a negative voltage is applied to the ion box 116*b* while a positive voltage is applied to the ion box 116*f*. As a result, when the density of the bar-like cigarette S is equal to the reference density, an amplifier 116*g* to which ionization currents are applied from the ion boxes 116*b* and 116*f* provides an output of the zero level, and when the density of the bar-like cigarette S is higher or lower than the reference density, the amplifier 116*g* provides a negative or positive output, respectively, Accordingly, at the output of the amplifier 116*g*, a signal is obtained which has a magnitude corresponding to a deviation of the density of the bar-like cigarette S from the reference density.

Reference is now made to FIG. 7 which illustrates a controlling circuit for the device according to the present invention, and in this figure, like parts or components are designated by like reference numerals to those of FIGS. 4 to 6.

As described in connection with FIG. 4, shredded tobacco T is attracted into and moved up within the chimney 100 and is then attracted into a layer on a bottom face of the perforated cigarette conveyor 103 located at the bottom of a suction chamber 102. The shredded tobacco thus layered is carried in a leftward direction in FIG. 4 and an excessive amount of the shredded tobacco is cut off or removed by means of a trimming disk 104*a* of the trimming device 104.

Thereafter, the shredded tobacco is carried to the first radio ray density detector 106 as shown in a dotted line, and the density is measured thereat. In particular, as described in connection with FIG. 5, radio rays emitted from the radio ray source 106*a* pass through the tobacco T and are received by the ion box 106*b*. Since a high voltage is applied to the ion box 106*b*, a weak ionization current is produced at an output of the ion box 106*b*. The weak current is amplified by the amplifier 106*i* and is then added to a reference signal from the reference voltage generator 200 and amplified by another amplifier 202. A signal produced at an output of the amplifier 202 is thus a voltage signal having a polarity and a magnitude corresponding to a deviation of a measured density from the reference desnity. Thereafter, the shredded tobacco T is wrapped into wrapping paper and then pasted and formed into a bar-like cigarette. The shredded tobacco in the form of a bar-like cigaratte S is advanced to the second radio ray density detector 116.

As described in connection with FIG. 6, in the detector 116, radio rays emitted from the radio ray source 116*a* pass through a bar-like cigarette S and are received by the ion box 116*b*. Meanwhile, radio rays emitted from the other radio ray source 116*d* pass through the reference density body 116*e* and are received by the ion box 116*c*. Since voltages of opposite polarities are applied to the ion boxes 116*b* and 116*f*, a voltage signal having a polarity and a magnitude corresponding to a deviation of a measured density of the bar-like cigarette S from the reference density is produced at the output of the amplifier 116*g*. An output of the amplifier 116*g* is amplified by an amplifier 204.

In summary, a deviation of the density of the bar-like cigarette S appears at the output of the amplifier 204 while a deviation of the density of the shredded tobacco T in the form of a layer appears at the output of the amplifier 202. Although the two outputs must essentially be identical with each other, actually some error appears between them since fine shreds are sucked into the suction chamber 102 through the holes formed in the perforated cigarette conveyor 103 even after the shredded tobacco T has left the first density detector 106 as hereinafter described.

The output of the amplifier 204 is inputted to another amplifier 208 to which an output of the amplifier 202 inverted by a further amplifier 206 is inputted in order to obtain a difference between the outputs of the amplifiers 204 and 202. Thus, at an output of the amplifier 208, a signal is obtained which is proportional to a difference between the output of the first radio ray density detector 106 and the output of the second radio ray density detector 116. When the output signal of the amplifier 208 is a value between two voltage values provided by voltage generators 210 and 212, comparators 214 and 216 both provide a low level output, and when the signal is otherwise not between the voltage values, either one of the outputs of the comparators 214 and 216 presents a high level so that a signal of a high level appears at an output 220 of an OR gate 218.

The output signal of the high level of the OR gate 218 indicates that there is an extraordinary difference appearing between two measured values of the two radio ray density detectors. Thus, the machine can be stopped or such an emergency can be indicated using such a signal of the OR gate 218. Accordingly, an amount of content tobacco can be assured for all of cigarettes produced, and appearance of a most dishonorable situation to cigarette produces that rejected products caused by a trouble should be shipped can be prevented beforehand.

The output of the amplifier 202 which outputs a measured value of the first radio ray density detector 106 is applied as a first signal to an adder 226 while the output of the amplifier 204 which outputs a measured value of the second radio ray density detector 116 is integrated by an integrator 222 and then adjusted for a gain by a amplifier 224 and is thus applied as a second signal to the adder 226 so that the first and second signals may be added to each other by the adder 226.

An output of the adder 226 is integrated by an integrator 228 and amplified by an amplifier 230 and is then inputted to an electric hydraulic servo value 232. The electric hydraulic servo valve 232 supplies, in accordance with a voltage supplied thereto, a flow of oil generated by a gear pump 234 alternatively to an upper or lower section of a cylinder 236 to move a piston 238 up or down within the cylinder 236. Up or down movement of the piston 238 is transmitted via a link 240, a shaft 242, another link 244 and a connecting rod 246 to move the trimming disk 104a of the trimming device 104.

The position of the trimming disk 104*a* is detected by a differential transformer 248. A signal of several kHz generated by an oscillator 250 is applied to the differential transformer 248, and a piston 238 is connected to a central core of the differential transformer 248 by way of a shaft 242 and a link 240. Accordingly, a signal appears at an output of the differential transformer 248 in response to up or down movement of the piston 238, and the signal is amplified by an amplifier 252. An output of the amplifier 252 is grounded at half wave portions thereof by a switch 254 which is operated by the output signal of the oscillator 250 while only the other half wave portions of the output of the amplifier 252 are smoothed by a low-pass filter 256 and are DC amplified by an amplifier 258. An output of the amplifier 258 is applied as a third input signal to the adder 226.

In the device having such a construction as described above, when a sum of the first and second inputs to the adder 226 is positive, that is, when an amount of content tobacco is too small, a voltage is generated at the output of the adder 226, and hence the output of the integrator 228 becomes gradually increased in the negative direction. As a result, the output of the amplifier 230 increases gradually in the positive direction so that the electric hydraulic servo valve 232 gradually changes a flow of oil to push up the piston 238 to lower the trimming disk 104*a* via the link 240, the shaft 242, the link 244 and the connecting rod 246 thereby to increase an amount of content tobacco. Simultaneously, an output appears at the differential transformer 248 so that the third input to the adder 226 is increased accordingly. Thus, the trimming disk 104*a* is lowered until the third signal becomes equal to a sum of the first and second signals. On the contrary, when an amount of content tobacco is too large, the device operates in the reverse polarities to those of the case described just above. The speed of such operation can be adjusted by changing the speed of integration by the integrator 228, and the extent of such operation can be adjusted by changing the gain of the amplifier 230.

With such a construction as described just above, the second signal, that is, a signal associated with the radio ray density detector 116, is obtained by integrating a density signal with the integrator 222. Meanwhile, the first signal, that is, a signal associated with the radio ray density detector 106, is proportional to a density signal. Accordingly, when there is a difference between the second and first signals, the second signal is integrated and becomes larger until finally it has a magnitude prevailing over the first signal although the first signal may prevail over the second signal within a short period of time. Therefore, an amount of content tobacco of cigarettes is determined and controlled by the first signal for fluctuations of a short period while it is determined and controlled by the second signal for fluctuations of a long period.

Figure 8:
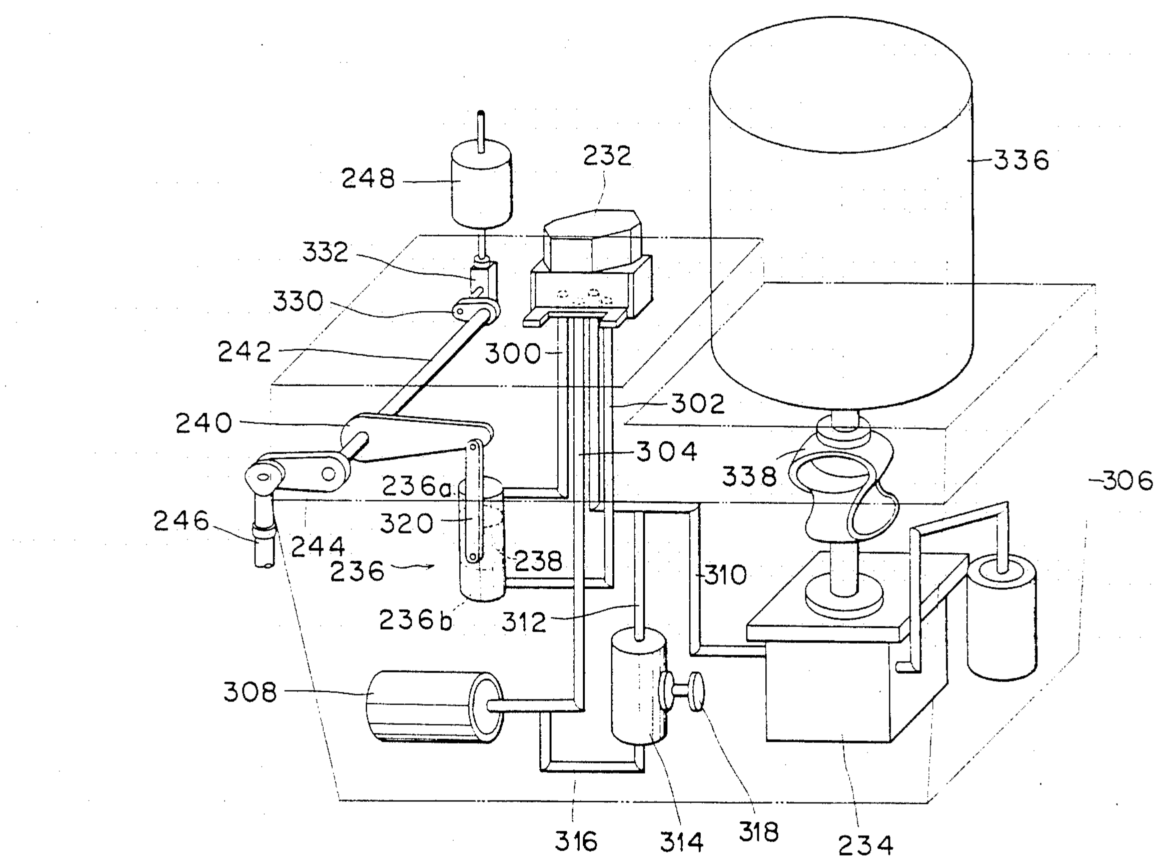
FIG. 8 is a perspective view showing details of a different portion of the machine of FIG. 4.

Referring to FIG. 8 which illustrates details of the driving device for driving the trimming disk 104*a*, the piston 238 is mounted for sliding up and down movement within the piston cylinder 236 which is secured to an outer casing, and when oil pressure is introduced into a cylinder chamber 236*a* through a pipe 330, the piston 238 is pushed down thereby while oil within another cylinder chamber 236*b* on the opposite side relative to the piston 238 is discharged into a tank passing through a pipe 302 and then a return pipe 304. On the contrary, when pressure oil is introduced into the cylinder chamber 236b via the pipe 302, the piston 238 is pushed up thereby while oil within the cylinder chamber 236*a* is discharged into the tank passing through the pipe 300 and the return pipe 304 in a similar manner. A filter 308 is provided at an exit of the return pipe 304.

The hydraulic pressure is maintained constant in the hydraulic system. When a hydraulic pressure higher than a preset pressure is applied thereto by the gear pump, a relief pipe 314 is operated via a pipe 312 branched from an intermediate portion of a pipe 310 extending from the gear pump 234 to the electric hydraulic servo valve 232 so that pressure oil is discharged into the tank through the return pipe 316 and the filter 308. Oil pressure within the hydraulic system is set or determined by adjusting a pressure adjusting screw 318.

Up and down movement of the piston 238 is effected by means of a connecting rod 320 pivotally connected to the piston 238. The other end of the connecting rod 320 is pivotally supported on the link 240 so that up and down movement of the piston 238 will pivotally rock the link 240 together with the shaft 242. The link 240 is fixedly mounted on the shaft 242 which is supported for rotation on the outer casing 306. Pivotal rocking motion transmitted to the shaft 242 will move, by way of the link 244 securely mounted on an end of the shaft 242, the connecting shaft 246 pivotally supported at the other end of the link 244 vertically up and down. The trimming disk 104a is moved up and down by up and down movement of the connecting shaft 246.

A link 330 is securely mounted at the other end of the shaft 242 so that pivotal motion of the shaft 242 will pivotally rock the link 330. Another link 332 is mounted on the link 330 so that pivotal rocking motion of the link 330 will move the link 332 up and down. The central core of the differential transformer 248 is secured to the link 332 so that the core may be moved by up and down movement of the link 332.

The differential transformer 248 is constituted such that when the core moves up, it produces a positive voltage in proportion, for example, to a distance of travel of the core, and on the contrary when the core moves down, it produces a negative voltage. In the present embodiment, a positive voltage is generated by the differential transformer 248 when the connecting shaft 246 is moved upwardly, and on the contrary when the connecting shaft 246 is moved downwardly, a negative voltage is generated by the differential transformer 248.

A motor 336 is connected to the gear pump 234 by way of a universal coupling 338.

As apparent from the foregoing description, according to the present invention, control of an amount of content tobacco can be attained wherein a responding speed of control of an amount of content tobacco of cigarettes is quick since a measured value directly behind a trimming device is used and accuracy of control is high since another measured value directly after formation of cigarettes is used.

Now, an examination is made of a ratio between a deviation of an average amount of content tobacco of cigarettes when controlled and a deviation of an average amount of content tobacco of cigaretes when not controlled, which ratio is regarded as an aim for judging merits and demerits of a control. While the ratio is 1/1.5 to ½ with a conventional cigarette making machine having a capacity to produce 4,000 cigarettes per minute, where a device according to the present invention is employed, the ratio becomes a good value of ⅓. This is apparent from the fact that a device according to the present invention has such a high speed that, for example, when an amount of content tobacco varies by 2 percent, correction will require only 200 milliseconds while correction in a conventional device requires 5 to 1 minute.

What is claimed is:

1. A content tobacco amount controlling device for use with a cigarette making machine for the type including a cigarette conveyor for attracting and conveying shredded tobacco thereon, a trimming device for removing an excessive amount of shredded tobacco conveyed by said cigarette conveyor to regulate an amount of content tobacco, and tobacco wrapping means for transferring the content tobacco trimmed by said trimming device onto continuous tobacco roll paper and for wrapping the content tobacco into the tobacco roll paper to make a bar-like cigarette, said content tobacco amount controlling device comprising:

a first radio ray density detecting means for irradiating with radio rays tobacco on said cigarette conveyor directly after the tobacoo has been trimmed by said trimming device and for measuring an amount of radio rays passing through the tobacco to produce an electric output signal representative of a difference between a measured density of the tobacco and a reference density;

a second radio ray density detecting means for irradiating with radio rays a bar-like cigarette made by said tobacco wrapping means and for measuring an amount of radio rays passing through the bar-like cigarette to produce an electric output signal representative of a difference between a measured density of a bar-like cigarette and a reference density;

a first integrating means connected to said second radio ray density detecting means for integrating an electric signal from said radio ray density detecting means;

an adding means connected to said first integrating means for adding an output of said first integrating to an output of said first radio ray density detecting means; and a second integrating means connected to said adding means for integrating an output of said adding means;

said trimming device being operated in response to an output of second integrating means to control an amount of content tobacco after trimming.

* * * * *